United States Patent

Rahman et al.

[11] Patent Number: 5,562,865
[45] Date of Patent: Oct. 8, 1996

[54] OXAZOLIDINE AND TETRAHYDROOXAZINE AMIDE SURFACTANTS

[75] Inventors: Mohammad A. Rahman, River Edge; Shang-Ren Wu, Mahwah, both of N.J.; Anthony Hung, New City, N.Y.

[73] Assignee: Lever Brothers Company, Division of Conopco, Inc., New York, N.Y.

[21] Appl. No.: 444,333

[22] Filed: May 18, 1995

[51] Int. Cl.$^6$ .................................................. C11D 3/28
[52] U.S. Cl. .................. 544/97; 548/215; 510/433; 510/500
[58] Field of Search ................. 544/97; 548/215; 252/542, 174.17

[56] References Cited

U.S. PATENT DOCUMENTS

| | | | |
|---|---|---|---|
| 2,662,073 | 12/1953 | Mehltretter et al. | 260/102 |
| 4,243,811 | 1/1981 | Teach | 548/215 |
| 4,319,031 | 3/1982 | Teach | 548/200 |
| 5,009,814 | 4/1991 | Kelkenberg et al. | 252/548 |
| 5,389,279 | 2/1995 | Au et al. | 252/108 |

FOREIGN PATENT DOCUMENTS

| | | |
|---|---|---|
| 1401768 | 7/1975 | United Kingdom . |
| 92/06157 | 4/1992 | WIPO . |

OTHER PUBLICATIONS

Bergmann, Chemical Reviews vol. 53, pp. 309–352 (1953) No Month Available.

*Primary Examiner*—Paul Lieberman
*Assistant Examiner*—Michael P. Tierney
*Attorney, Agent, or Firm*—Ronald A. Koatz

[57] ABSTRACT

The present invention relating to novel oxazolidine and tetrahydrooxazine amide surfactants and to processes for making the surfactants. These are cyclic surfactants having good solubility and which are readily biodegradable.

7 Claims, No Drawings

OXAZOLIDINE AND TETRAHYDROOXAZINE AMIDE SURFACTANTS

BACKGROUND OF THE INVENTION

The present invention relates to novel oxazolidine amide (5 member ring) and tetrahydrooxazine amide (6 member ring) surfactants and to methods for preparing the surfactants. These surfactants are biodegradable, sugar-based surfactants.

It has in recent years become a highly desirable goal in the art to find surfactants which are environmentally friendly and preferably not tremendously expensive. Carbohydrate based surfactants are good candidates in this regard because they offer the possibility of cheap, renewable and biodegradable surfactants.

Several carbohydrate based amide surfactants are known in the art.

In U.S. Pat. No. 5,389,279 to Au et al., for example, there are taught certain aldobionamide compounds. These compounds are structurally different than the compounds of the subject invention.

U.S. Pat. No. 5,009,814 to Kelkenberg et al. provides N-polyhydroxyalkyl fatty acid amides used as thickeners in aqueous surfactant systems and having the formula:

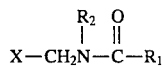

wherein $R_1$ is alkyl, $R_2$ is hydrogen, alkyl or hydroxy alkyl and X is a polyhydroxy group.

A series of Procter and Gamble references teach various compositions which comprise polyhydroxy amides. WO-92/06172, for example, teaches built liquid detergent compositions containing polyhydroxy fatty acid amides. There are about 20 references reciting various compositions containing the same polyhydroxy amides.

The polyhydroxy fatty acid amides are generally linear structures (i.e., wherein the polyhydroxy group is derived from monosaccharides such as in the case of N-methyl glucamide). Such linear structures would be expected to have strong intermolecular interactions leading to, for example, higher Krafft points and therefore to be less soluble than cyclic surfactants such as the compounds of the invention (Krafft point is a measure of solubility; specifically, it is the temperature at which the solubility of the nonionic surfactant becomes equal to its critical micelle concentration). Even if the polyhydroxy amide is a disaccharide, the compounds still have an extended linear structure within the molecule which differs from the compounds of the invention.

Polyhydroxy fatty acid amides with a reverse amide link from the polyhydroxy fatty amides noted above (e.g., N-alkyl gluconamides of general structure $HOCH_2(CHOH)_4CONHR$) are also known in the art, for example, in U.S. Pat. No. 2,662,073 to Mehltretter et al. As noted, these are either linear structures which would be expected to have higher Krafft points (i.e., be less soluble) than cyclic compounds; or they have extended linear structures within the molecules which would also be expected to raise the Krafft point.

Thus, it would be advantageous to find a carbohydrate based surfactant with a structure providing greater solubility. In addition, it is always desirable to find a novel, carbohydrate surfactant, whether or not it has a cyclic structure.

SUMMARY OF THE INVENTION

The present invention relates to novel carbohydrate surfactants having one of the general structures set forth as in compound I below:

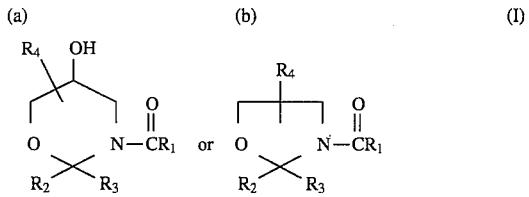

wherein:

$R_1$ is a linear or branched, saturated or unsaturated alkyl group (i.e., alkyl or alkenyl) having 1 to 50 carbons, preferably 1 to 40, more preferably 8 to 24 carbons;

$R_2$ and $R_3$ are hydrogen or a linear or branched, saturated or unsaturated alkyl group (i.e., alkyl or alkenyl) having 1 to 50 carbons, preferably 1 to 40, more preferably 8 to 24; and;

$R_4$ in general, will be whatever group was originally attached to the reducing sugar prior to the reductive amination which formed the intermediate amino sugar (e.g., glucamines or glucosamines) which intermediate amino sugars are in turn cyclized to form either the 5 member oxazolidine or 6 member tetrahydrooxazine prior to amidation. It should be noted from the structure that the $R_4$ group may be attached at varying places in the ring depending on the starting reducing sugars or amino sugars.

$R_4$, for example, may be hydrogen in the case of the 6 member ring or $CH_2OH$ in the case of the 5 member ring when the starting sugar is glyceralaldehyde.

Suitable reducing sugars (starting sugars) which will define $R_4$ include glucose, fructose, maltose, lactose, galactose, mannose, xylose, erythritose and as noted above, glyceraldehyde. Starting sugars could also be the amino sugars such as glucamine or glucosamine. As raw materials, high dextrose corn syrup, high fructose corn syrup, and high maltose corn syrup can be utilized as well as the individual sugars listed above. These corn syrups may yield a mix of sugar components for use in yielding the final $R_4$. It should be understood that it is by no means intended to exclude other suitable raw materials.

$R_4$ preferably will be selected from the group consisting of $—(CHOH)_n—CH_2OH$ where n is an integer from 1 to 5. Most preferred depends on whether the resulting compound is compound (a) or (b). In the case of (a), preferably n=2 and in the case of (b), preferably n=3. Depending on the starting sugar, $R_4$ can be any saccharide or residual saccharide structure.

In a specific embodiment of the invention, the compound has one of the following structures:

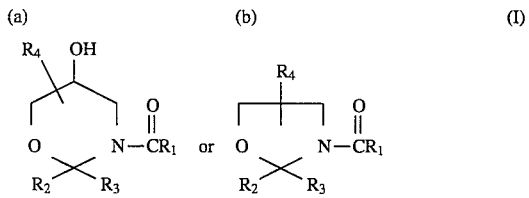

wherein $R_4=—(CHOH)_{n'}—CH_2OH$, where, when it is structure (b), n' equals 3; and, when it is structure (a), n' equals 2; and $R_1$, $R_2$ and $R_3$ are as defined as in compound (I), (a) and (b) above.

3

Other preferred embodiments of the invention include, but are not limited to (1) $R_2=R_3$=hydrogen; and $R_1=C_{11}$ to $C_{17}$; and
(2) $R_2$=hydrogen; $R_1=CH_3$; and $R_3=C_{11}$ to $C_{17}$.

One requirement of the invention is that the combination of $R_1$ and $R_2$ and $R_3$ should equal $C_8$ or greater, preferably $C_8$ to $C_{50}$, more preferably $C_{12}$ to $C_{30}$.

DETAILED DESCRIPTION OF THE INVENTION

The present invention relates to novel carbohydrate surfactants having one of the formula set forth below:

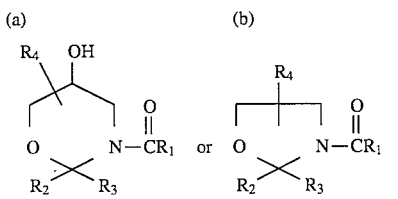

wherein:

$R_1$ is a linear or branched, saturated or unsaturated alkyl or group (i.e., alkyl or alkenyl) having 1 to 50 carbons, preferably 1 to 40, more preferably 8 to 24 carbons;

$R_2$ and $R_3$ are hydrogen or linear or branched, saturated or unsaturated alkyl group having 1 to 50 carbons, preferably 1 to 40, more preferably 8 to 24; and $R_4$ is whatever group was originally attached to the reducing sugar prior to the reductive amination which formed the intermediate amine sugar (the amino sugar, e.g., glucamine or glucosamine, may also be used directly as a bulk or preformed starting material) which starting or intermediate amino sugar is in turn cyclized to form the 5-member oxazolidine or 6-member tetrahydrooxazine prior to amidation.

The $R_4$ group may be attached at various locations in the ring, as noted from the structure, depending on the starting sugar or amino sugar.

$R_4$, for example, may be hydrogen or $CH_2OH$ when starting sugar is glyceraldehyde, depending on whether the 5 or 6 membered ring is formed (i.e., hydrogen in the case of 6 member ring). Suitable reducing sugars which define what $R_4$ will ultimately become include glucose, fructose, maltose, lactose, galactose, mannose, xylose, erythritose, as well as glyceraldehyde. The starting material, as noted above, may also be a bulk or pre-made amino sugar product such as glucamine or glucosamine. As raw materials, high dextrose corn syrup, high fructose corn syrup, and high maltose corn syrup can be utilized as well as the individual sugars listed above. These corn syrups may yield a mix of sugar components for use in yielding the final $R_4$. It should be understood that it is by no means intended to exclude other suitable raw materials. $R_4$ preferably will be selected from the group consisting of $-(CHOH)_n-CH_2OH$ where n is an integer from 1 to 5, inclusive. Most preferred depends on whether the resulting compound is the five or six member ring compound. In the five member ring, n=3 and, in the six member ring, n=2. Again, depending on the starting sugar or amino sugar, $R_4$ can be polysaccharide or residual polysaccharide structure.

In one embodiment of the invention, the compound has the following structure:

4

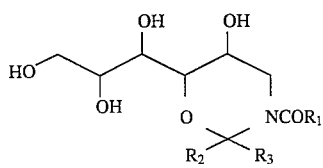

wherein $R_1$=a $C_1$ to $C_{50}$ alkyl group as defined above; and $R_2$, $R_3$=H or $C_1$ to $C_{50}$ alkyl group as defined above.

$R_1$ plus $R_2$ plus $R_3$ should be at least $C_8$, preferably $C_{12}$ to $C_{30}$, more preferably $C_{12}$ to $C_{24}$.

In a preferred embodiment of the invention, $R_2$ and $R_3$ are hydrogen or $C_1$ to $C_4$ alkyl and $R_1$ is a $C_8$ to $C_{24}$ straight chain.

In another preferred embodiment, either $R_2$ and $R_3$ is $C_8$ to $C_{24}$ alkyl and $R_1$ is a $C_1$ to $C_6$ short chain alkyl group. While not wishing to be bound by theory, it is believed that enhanced surfactancy properties will be realized if, when either one of $R_1$, $R_2$ or $R_3$ is long chained, then the others are short chained (i.e., only one long chain is required).

In another preferred embodiment the compound has the following structure:

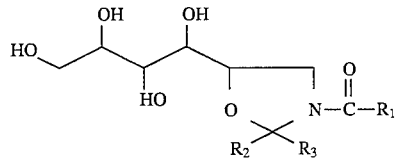

wherein $R_1=C_1$ to $C_{50}$ alkyl as defined above;

$R_2$, $R_3$=H or $C_1$ to $C_{50}$ alkyl group as defined above.

$R_1$ plus $R_2$ plus $R_3$ should be at least $C_8$, preferably $C_{12}$ to $C_{30}$, more preferably $C_{12}$ to $C_{24}$ Preferably:

$R_1=C_1$ to $C_4$ straight chain alkyl; and $R_2$ or $R_3$ is $C_8$ to $C_{24}$ straight chain alkyl In another embodiment of the invention, the present invention is concerned with a method for preparing the novel surfactants described above.

General Method for the Preparation of Oxazolidines Amide

The oxazolidine amides were synthesized by the reaction of available sugar amine such as, for example, glucamine (e.g., 1-Amino-1-deoxysorbitol) with various long chain aldehydes (e.g., fatty aldehyde). Glucamine is synthesized by reductive amination of glucose and ammonia. The sugar amine (e.g., glucamine) was dissolved in a solvent such as anhydrous methanol and refluxed for 12–24 hours with stirring to form a clear solution. Other suitable solvents include ethanol, propanol, isopropanol, ethylene glycol, propylene glycol, ethylene glycol monomethyl ether and diethylene glycol. Equimolar amounts of fatty aldehyde were added and refluxed in solvent (e.g., anhydrous methanol) with an acid catalyst. Suitable catalyst include, but are not limited to sulfonic acids, such as p-toluenesulphonic acid, methanesulfonic acid or alkyl benzenesulfonic acid; and acid resins such as Amberlite IR - 120, (ex., for example, Aldrich). The amidation step (in the same reaction vessel) involved cooling the reaction to about 10° C. to 25° C. with an ice bath and adding 1.0 to 1.5 equivalent of anhydride. Suitable anhydride include any component of formula:

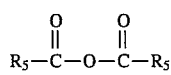

where $R_5$ is $C_1$ to $C_{30}$, preferably $C_1$ to $C_4$

The solvent was removed under reduced pressure and the crude product purified by washing with, for example, hexanes and recrystallization in acetone or ethyl acetate.

General Methods for the Preparation of Tetrahydrooxazine Amides

Sugar amine (e.g., glucamine) was dissolved in refluxing solvent such as methanol for 2 to 4 hours with stirring until solution turned clear. Other solvents which could be used include ethanol, propanol, isopropanol, ethylene glycol, propylene glycol, monomethyl ether and diethylene glycol. The solution was cooled to room temperature and an aidehyde (e.g., formaldehyde or short chain aidehyde) solution was added. The reaction was allowed to go for about 24 hours and then all the solvent was removed under reduced pressure. This syrupy intermediate was not purified and was used for the next step. This material was dissolved in a solvent system (e.g., mixture of a 2:1 Dimethylformamide;pyridine solution) and acylated with the appropriate long chain acid chloride (1.0 to 1.5 equivalents) at 0° C. The product was purified by extraction and recrystallized in the appropriate solvent.

Choice of aidehyde and choice of anhydride (or acyl chloride) determine length Of $R_2$, $R_3$ and $R_1$, respectively. These are generally chosen such that, wherein $R_1$ is short chained (e.g., $C_1$ to $C_6$), $R_2$ and/or $R_3$ will be long chained (e.g., $C_8$ to $C_{40}$) preferably $C_{12}$ to $C_{30}$, more preferably $C_{12}$ to $C_{24}$; and when $R_1$ is long chained ($C_8$ to $C_{40}$), $R_2$ and/or $R_3$ are hydrogen or short chain alkyl. While not wishing to be bound by theory, this is believed to be desirable in terms of optimizing the surfactancy of the molecule. $R_1$ plus $R_2$ plus $R_3$ should be at least $C_8$ or greater, preferably $C_{12}$ or greater.

Unless stated otherwise, all percentages which may be mentioned are percentages by weight.

The following examples are intended to further illustrate the invention and are not intended to limit the invention in any way.

The reagents used in preparation of the oxazolidine acetamide surfactants for use in detergent compositions are as follows:

Reagents: D-Glucamine (Janssen Chimica); dodecyl aidehyde (Aldrich); tetradecyl aidehyde (Aldrich); acetic anhydride (Fisher Scientific).

EXAMPLE 1

Preparation of $C_{12}$ Oxazolidine Acetamide

In a 2-neck 2-liter round bottom flask was added D-Glucamine (30g, 0.166 moles) and 1.5 liters of anhydrous methyl alcohol. The reaction was stirred (via magnetic stir bar) and refluxed using an oil bath. After vigorous refluxing, the solution went clear and the reaction was cooled to room temperature. Dodecyl aidehyde (33.05g, 0.179 moles) and 1.1 g of anhydrous p-toluenesulphonic acid was added to the reaction. The reaction was refluxed for 24 hours and then cooled to 10° C. using an ice bath. Addition of acetic anhydride (17.80 g, 0.174 moles) soon followed and the reaction was allowed to run at room temperature for an additional 12 hours.

The reaction was worked up by removal of the methanol solvent. Recrystallization in acetone gave approximately 65 g of crude material. Further analysis indicated that the this material contained two diasteromers as analyzed by NMR and mass spectrometry. The two pure diasteromers were isolated by chromatrography under the following conditions:

Column chromatography was done on a column packed with $C_{18}$- (Regis) Bodman Biochrom. 1040 using ODS FEC PQ packing material. The solvent used was 55:45 $CH_3CN:H_2O$. After separation the purity was analyzed as follows on an HPLC.

A column having the dimension spherisorb hexyl 5 µm×15 cm×4.6 cm was packed with Spherisorb hexyl using the mobile phase containing the following solvent: 30%/30%/40% $CH_3OH/CH_3CN/H_2O$ (volume percent). 14 g/L NaClO4 (Sodium perchlorate) was used in the solvent system and column temperature was 35° C.

One of the diastereomers showed the following characteristics:

$^{13}C$ NMR in $CD_3OD$: 14.48, 21.96, 23.22, 23.75, 24.36, 24.44, 30.50, 30.65, 30.74, 30.81, 33.09, 34.20, 64.73, 71.95, 72.31, 72.36, 72.46, 72.69, 80.22, 80.56, 90.58, 90.81, 170.10, 170.73.

EXAMPLE 2

Preparation of $C_{14}$ Tetrahydrooxazine Amide

A solution of glucamine (20 g) and 500 ml of methanol was heated for 2 hours under reflux. The solution was cooled to room temperature and then 37% formaldehyde solution (10.8 ml) was added followed by addition of p-toluenesulphonic acid (2 g). The reaction mixture was stirred at room temperature overnight. The solvent was removed by azeotropic distillation with toluene. The crude oxazolidine was not purified.

To a solution of tetrahydrooxazine of glucamine (22 g, .113 moles) in dry dimethylformamide (50 ml) was added dry pyrridine (25 ml). The solution was cooled to 0° C. using an ice bath. Myristoyl chloride (35.59 ml, .13 moles) was added portionwise over a 15 minute period. The reaction was stirred for 3 hours at 0° C. and then room temperature overnight. Ice was added to the reaction and then extracted with methylene chloride (3×200 ml) and then dried over anhydrous sodium sulfate. Filtering the sodium sulfate and removal of the solvent gave the crude product which was further recrystallized from acetonitrile:water (8:2). The pure product was analyzed by NMR, IR, and mass spectrometry.

We claim:

1. A compound selected from the group consisting of:

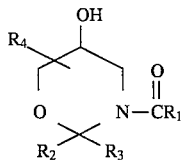
(a)

or

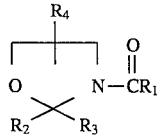
(b)

wherein:

$R_1$ is a linear or branched, saturated or unsaturated alkyl group having 1 to 50 carbons;

$R_2$ and $R_3$ are hydrogen or a linear or branched, saturated or unsaturated alkyl group having 1 to 50 carbons; and $R_4$ is —$(CHOH)_{n'}$—$CH_2OH$; wherein n' is 0 to 5.

2. A compound according to claim 1, wherein the starting sugar from which $R_4$ is derived is selected from the group consisting of glucose, fructose, maltose, lactose, galactose, mannose, xylose erythritose and glyceraldehyde.

3. A compound according to claim 1, wherein the starting amino sugar from which $R_4$ is derived is glucamine or glucosamine.

4. A 6-membered tetrahydrooxazine compound according to claim 1, wherein $R_4$ is —$(CHOH)_{n'}$—$CH_2OH$; and wherein n' 1 to 5.

5. A 5-membered oxazolidine compound according to claim 1, wherein $R_4$ is

—$(CHOH)_{n'}$—$CH_2OH$; and wherein n'=1 to 5.

6. A compound according to claim 4, wherein $R_2=R_3=$ hydrogen and $R_1=C_{11}$ to $C_{17}$.

7. A compound according to claim 5, wherein $R_2$=hydrogen, $R_2=CH_3$ and $R_3=C_{11}$ to $C_{17}$.

* * * * *